United States Patent [19]

Gilford et al.

[11] 4,236,825

[45] Dec. 2, 1980

[54] AUTOMATIC MONOCHROMATIC LIGHT ABSORBANCE MEASUREMENT ANALYZER

[75] Inventors: Saul R. Gilford, Oberlin; Robert J. Emary, Wakeman; Glen A. Carey, North Ridgeville, all of Ohio

[73] Assignee: Gilford Instrument Laboratories, Inc., Oberlin, Ohio

[21] Appl. No.: 929,987

[22] Filed: Aug. 1, 1978

[51] Int. Cl.³ ............................................. G01N 21/25
[52] U.S. Cl. ........................................ 356/414; 422/63
[58] Field of Search ......................... 356/409, 414, 244; 422/63, 65; 250/576, 328

[56] References Cited

U.S. PATENT DOCUMENTS

| | | | |
|---|---|---|---|
| 3,597,161 | 8/1969 | Greiner | 422/65 |
| 3,622,279 | 11/1971 | Moran | 250/576 X |
| 3,802,782 | 4/1974 | Natelson | 356/409 |
| 3,917,455 | 11/1975 | Bak et al. | 422/65 X |
| 3,985,507 | 10/1976 | Litz et al. | 356/244 X |
| 3,985,508 | 10/1976 | Williams | 422/65 |
| 4,058,367 | 11/1977 | Gilford | 422/63 |

*Primary Examiner*—John K. Corbin
*Assistant Examiner*—Bruce Y. Arnold
*Attorney, Agent, or Firm*—Baldwin, Egan, Walling & Fetzer

[57] ABSTRACT

A method of and apparatus for automatically taking monochromatic light absorbance measurements on a plurality of fluid samples such as serum. The fluid samples to be processed are contained in a vessel having a plurality of curvettes into each of which is disposed a fluid sample to be analyzed and which vessel is on a processing path and moved by a unique drive belt mechanism capable of providing a plurality of movements to the vessel in different directions and selectively to a first position or station whereat the cuvettes in said vessel are washed and evacuated of any unbound materials and thence to a second station whereat a reagent is sequentially and serially added to each of the cuvettes, after which the fluid sample in each cuvette is exposed to a monochromatic light absorbance measuring device straddling the track at said second position and a spectroanalysis is made thereof. The drive belt is actuated by a synchronous motor programmed to selectively position the cuvettes in predetermined, timed sequence first at the wash and evacuate station and thence at the reagent additive and analysis second station. The apparatus in coaction with the motor may be automatic and/or manually operable whereby a very large number of fluid samples may be very quickly analyzed for mass testing of large populations for highly infectious diseases.

8 Claims, 8 Drawing Figures

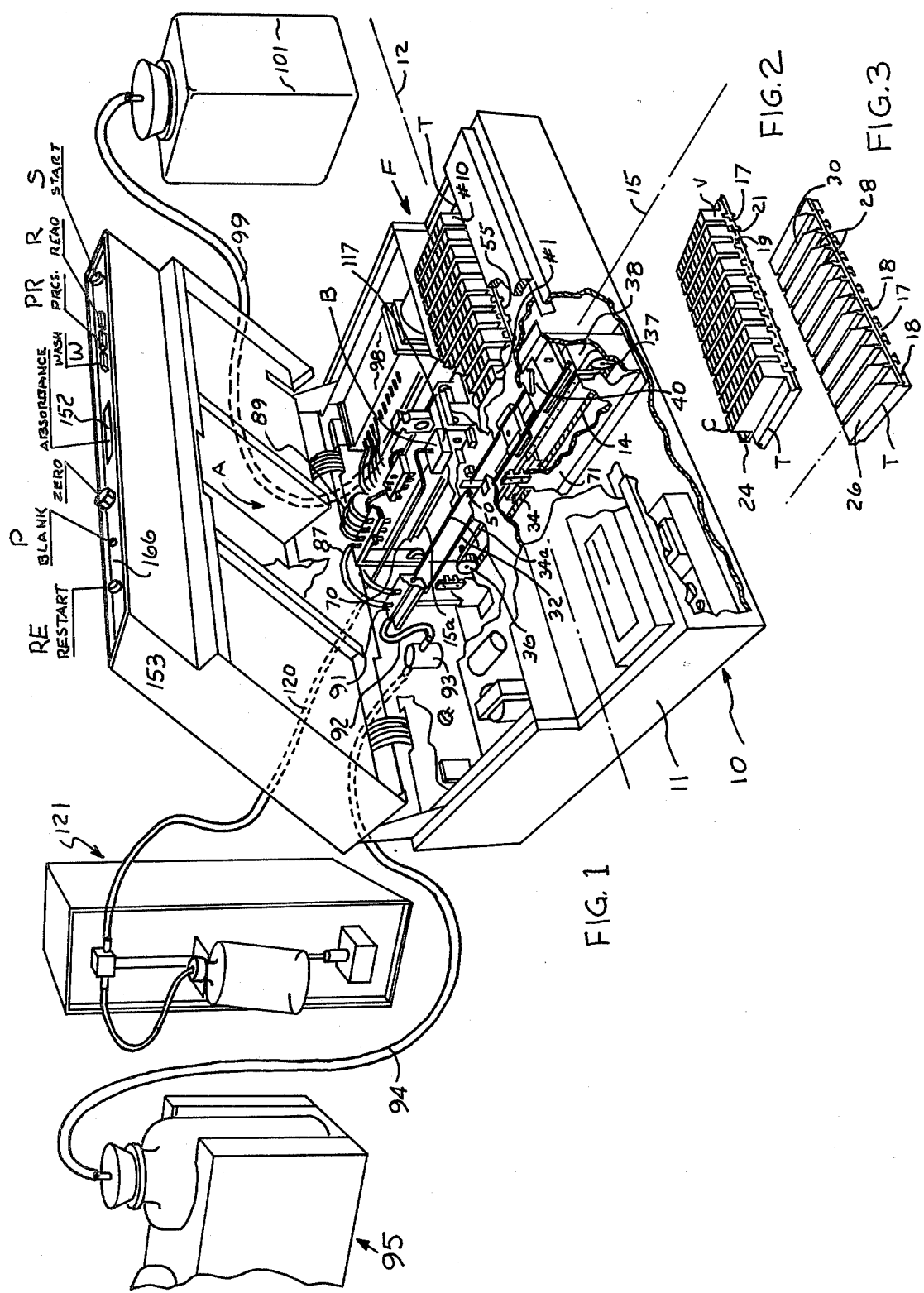

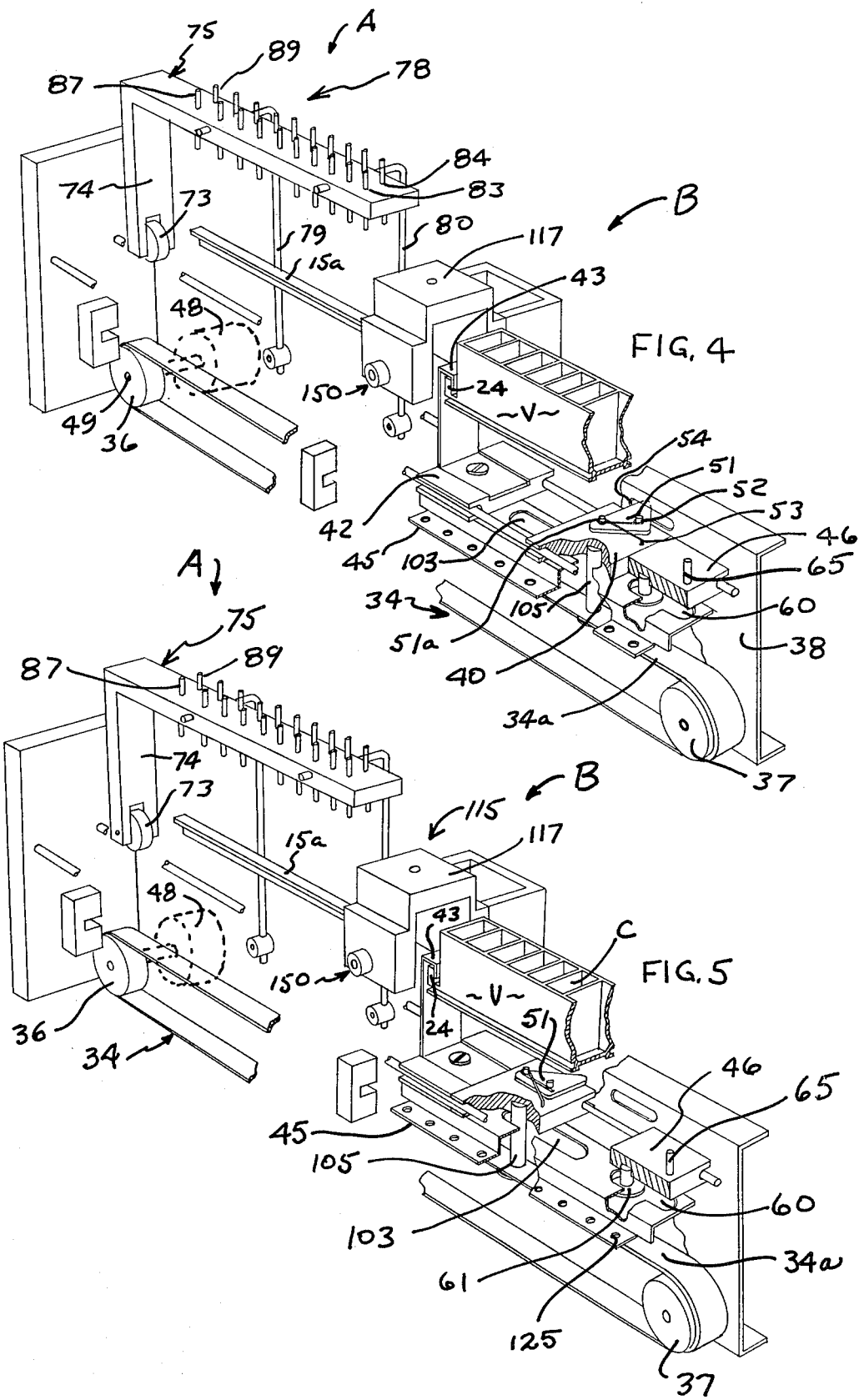

AUTOMATIC MONOCHROMATIC LIGHT ABSORBANCE MEASUREMENT ANALYZER

BACKGROUND OF THE INVENTION

This invention relates to analyzing apparatus in which a fluid sample is to be tested. While the invention herein is primarily related to the testing of biological samples such as serum, it is not intended to be so restricted in its utility.

The method and analyzing apparatus of the present invention provides a relatively simple, automatic and reliable testing of individual body fluid samples of a substantial number of patients suspected of having contracted a contagious disease such as, for example, gonorrhoeae, Rubella and other kinds of infectious diseases, and to also enable a mass population screen testing for said disease to be easily undertaken.

The present system is primarily designed to detect and measure infectious disease antigens and antibodies by the enzyme-linked immunosorbent assay indirect method as is described in the publication "The Enzyme Linked Immunosorbent Assay (ELISA)" by Voller, A., Bidwell, D. E. and Bartlett, A., published by Flowline Publications, Guernsey, Europe. The instrument system is designed to carry out the test protocol described by this publication, and typical tests performed with the subject analyzer, while not limited thereto, include digoxin, gonorrhea, hepatitis, Rubella, T3 and T4.

Merely for purposes of the present disclosure, the method and instrument apparatus of the present invention will be herein described for detection of infectious gonorrhoeae.

The infection caused by the organism Neisseria gonorrhoeae commonly known as Gonorrhea is a venereal disease of an extremely widespread nature in humans. The disease usually manifests itself by a visible discharge in males but frequently is undetected and undetectable by external symptoms in females infected therewith. Heretofore, the only reliable mode of detection of infection has been by culturing discharges of mucus fluids believed to contain the organism. Such cultures take a period of more than one day to grow. Because of the social opprobrium attached to the disease and the reluctance of many persons infected therewith to return to the test clinic, it has long been desirable to provide a screening method which can give a reliable indication of possible infection or noninfection during a time for which it is reasonable to require the test subject to remain in the clinic.

SUMMARY

For detecting infectious gonorrhoeae, the present method and apparatus encompasses utilizing a cuvette or cell onto which is coated the antigen or antibody of interest, i.e., Neisseria gonorrhoeae.

The patient's serum that is suspect is then manually added to this wetted antigen in the cuvette and this wetted mixture is then incubated for a period of time, as is set forth more fully in the aforesaid publication, during which incubation interval a binding reaction occurs between the antigen initially in the cuvette and that which is of interest in the patient's serum.

After incubation, the cuvette is again placed into the instrument and located at the first instrument station and the cuvette is aspirated to remove any unbound materials therein.

The cuvette is then moved to a second instrument station whereat a conjugate reagent is added and which contains an enzyme that binds to the antigen or antibody of interest and also to the other materials in the cuvette.

The cuvette is then again incubated to enable a complete reaction to occur.

The cuvette is then returned to the first instrument station whereat it is washed and aspirated to remove any unbound materials following which a substrate is added which is acted upon by the attached enzyme producing a characteristic photometrically measurable absorbance change.

The cuvette is then positioned at the second instrument station whereat it is subjected to a photometer analysis whereby the antibody-antigen enzyme complex of interest provides a particularly characteristic response which indicates the presence or absence of the infectious disease. This response may be visually indicated as well as being permanently recorded in a printed record.

A plurality of individual cuvettes or cells, each accommodating a patient's serum, are preferably contained in a single vessel, such as for example a group of ten cuvettes.

The instrument of the present invention encompasses a trackway along which the cuvette vessel is movable selectively into a plurality of instrument stations.

Each cuvette or cell preferably has suitable sample identification which corresponds to the individual patient so that the resultant test may be identified to its corresponding source.

A novel and unique vessel drive mechanism is programmable by a suitable control means to automatically move the cuvette vessel along the instrument trackway sequentially to the instrument stations, and in a preselected combination thereof.

For example, the drive mechanism may be programmed to move the cuvette vessel initially to the wash and vacuum station (first station), and subsequently to locate each cuvette or cell individually and serially to the reagent dispensing and measuring station (second station).

Alternatively, the drive mechanism may be programmed to locate the cuvette vessel initially at the reagent dispensing and measurement station whereat reagent dispensing and absorptive measurements are individually and serially undertaken on each cuvette or cell of said vessel.

Further, the drive mechanism may be programmed to merely initially carry the cuvette vessel to the wash and vacuum station whereat each cuvette or cell is washed and evacuated after which the vessel is returned to the trackway entrance for further processing or ultimate disposal.

Other combinations may be readily realized by one skilled in the art and the foregoing programs are merely illustrative and not intended to be restrictive.

BRIEF DESCRIPTION OF THE DRAWINGS

FIG. 1 is a perspective view, shown partly in section, of the apparatus encompassing the present invention;

FIG. 2 is a perspective view showing a plurality of cuvette vessels being carried on a tray and positionable for presentation to the apparatus;

FIG. 3 is a perspective view of the underside construction of a tray for carrying a plurality of cuvette vessels;

FIG. 4 is a perspective side view of the drive mechanism with portions of the frame cut away to expose underlying parts;

FIG. 5 is a partial side view of the drive mechanism with the drive block thereof actuated to its tray alignment position;

DESCRIPTION OF THE PREFERRED EMBODIMENT

Figure 6:
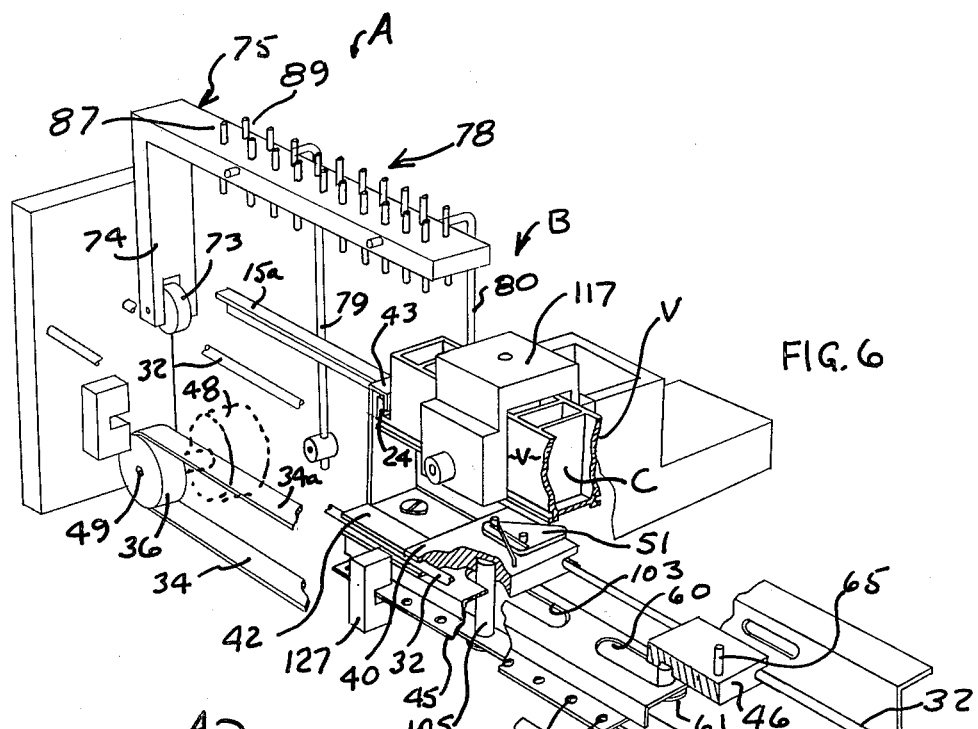
FIG. 6 is a partial side view similar to FIG. 5 and with the drive block in an intermediate position whereat it abuts against the coupler block to initiate moving a cuvette vessel through the entranceway of the trackway.

With reference directed to FIG. 1, the apparatus of the present invention is identified in its entirety at 10 and is seen to include a box-like base 11 of rectangular configuration and defining a guideway 12 extending longitudinally along and adjacent to the front of the base.

Approximately midway along the guideway 12, drive mechanism as identified at 14, is positioned within the base 11, extending perpendicular to the guideway 12 and extending rearwardly therefrom and in planar relation to define trackway 15 along which the cuvette vessel V is carried.

Positioned along the trackway 15 are a plurality of work stations such as for example as identified at A (first station) and B (second station) whereat predetermined processes i.e. wash and vacuum and reagent dispensing and measurement respectively may be performed on the sample fluid contained in each cuvette or cell C in the vessel V.

In the present embodiment of apparatus only two work stations A and B are illustrated but it is contemplated that additional work stations may be selectively positioned along the guideway 15 at which other processes may be performed.

As best seen in FIGS. 2 and 3, a plurality of vessels V are carried on each tray T. In the present embodiment ten (10) vessels V are thus carried, each vessel having ten (10) cuvettes or cells, each tray and vessel assembly thus accommodating one hundred samples.

Tray T is rectangular in overall configuration, and as seen in FIG. 2 is formed with a series of ten (10) channels 17 extending transversely of the longer sides thereof, and in equal spaced relation to each other. Each channel 17 is bounded on opposite sides by overlapping shoulders 18 which are intended to overlie complementary ledges 19 formed on opposed sides of an elongated keyway 21 located on the underside of the base of the vessel V.

As best seen in FIG. 2 each of the vessels V is releasably disposed on the upperside of the tray T by extending its keyway 21 into one of the channels 17 and sliding the same therethrough until the vessel is centrally located on said tray and extending transversely thereacross.

One end of each vessel V is provided with an upstanding coupling element 24 and extending outwardly therefrom.

As seen in FIG. 3, the underside surface 26 of tray T is formed with a series of cam surfaces 28, each of which opens to one longitudinal edge of the tray and projects linearly and angularly therefrom toward a groove or slot 30 which extends transversely across the tray. There is a groove or slot 30 for each vessel position wherein the longitudinal center line of the groove 30 is in alignment with the longitudinal center line of the vessel V at each respective vessel position, the purpose of which will be later explained.

Each tray T and vessel V unit is placed in the guideway 12 as seen in FIG. 1 so that the vessel V at vessel position #1 is closely adjacent the entrance to trackway way 15 with the upstanding vessel coupling element 24 disposed in the manner depicted in FIG. 2, and with the cam surfaces 28 facing said trackway entrance.

As shown herein the tray and vessel unit is manually placed in the guideway 12 but it is also contemplated that this could be accomplished by a suitable conveyor means.

With the unit thus located, the drive mechanism 14 may be actuated to extract the vessel then located at the trackway entrance and to carry the same through said trackway at which time the work functions are performed thereon.

To accomplish this, reference is directed to FIGS. 1, 5-8 which best illustrate the elemental assembly of the drive mechanism without the exterior supporting framework therefor.

As seen in FIG. 1, the drive mechanism comprises a pair of rod members 32 disposed in parallel-spaced relation and extending from the front of the instrument base 10 and rearwardly therefrom to define the trackway 15.

Positioned underneath the rod members 32 is an endless flexible drive belt 34 extending longitudinally therewith and supported between drive pinion 36 and support pinion 37, respectively carrried on wall 38. As seen, the belt 34 and pinions 36 and 37 are provided with complementary teeth to enable positive drive for the belt.

Securely attached to the upper run 34a of belt 34 and movable therewith through trackway 15, is a drive block 40 which straddles the rod members 32 and slidably moves therealong in response to belt movement.

A coupler block 42 similarly straddles the rod members 32 being free to slide therealong ahead of the drive block 40 as viewed in FIG. 1 from the front of the instrument and looking rearwardly along trackway 15. As seen in FIG. 4, a pickup element 43 is attached to the coupler block 42 and is intended to project downwardly and over the upstanding coupling element 24 of the vessel V located at the trackway entrance.

A position indicator plate 45 is securely fastened to the underside of the coupler block 42 and extends along and underneath the rod members 32 and under drive block 40 and a third block similarly supported on said rod members 32 and referred to herein as a retainer block 46.

Motor 48 is drivingly connected by shaft 49 to drive pinion 36 and is operable to move the upper belt run 34a selectively in opposite directions along trackway 15 and carry the drive block 40 therewith.

As seen in FIGS. 1 and 4, the drive mechanism is mounted in the housing 11 so that the blocks 40, 42 and 46 are positioned beneath the vessel tray T.

A plate 51 is swingably mounted on the upper face of the drive block 40 and carries an upstanding pin 52 thereon. As seen in FIG. 1, the plate 51 is positioned in its "start" position whereat an end adjacent pin 52 is spring biased by spring 53 to project partially into slot 54 formed in supporting wall 38. In this position, pin 52 is located slightly forwardly of the rear longitudinal edge 55 of the tray T.

With the assembly disposed as shown in FIGS. 1 and 4, and with actuation of the motor 43 to move the drive block 40 in the "in direction" along trackway 15, the plate 51 is initially swung in a clockwise direction about its pivot 51a to locate pin 52 within the area of the cam 28 which immediately underlies the vessel V located at or closely adjacent to the trackway entrance.

With the movement of drive block 40 continuing in the "in direction" pin 52 is carried into engagement with cam 28 whereby the tray T is moved in the forward direction F along the guideway 12 sufficiently to move the upstanding coupling element 24 behind and underneath the depending pickup element 43 as seen in FIG. 4.

Continued movement of drive block 40 brings it into abutment with coupler block 42 to thereby move it along the rod members 32 also in the "in direction". Because of the inter-coupling between coupling element 24 on the vessel V and the pickup element 43 on block 42, the vessel V is removed from the tray T and carried into and along the trackway 15.

As the coupler block 42 is moved by drive block 40, the position indicator plate 45 is carried therewith.

As best seen in FIGS. 4 and 5, this plate 45 is provided with an elongated slot 60 extending longitudinally therealong and into which slot extends a follower pin 61 projecting downwardly from the underside of the retainer block 46. This assembly thus defines a lost motion connection between the retainer block 46 and plate 45 such that as the plate 45 is carried by the drive block 40 in the "in direction" along trackway 15 the pin 61 is engaged by the rearward end of the slot 60 whereby the retainer block 46 is then propelled along with the drive block 40.

A retainer pin 65 is mounted on the upper surface of the retainer block 46 and as the block begins to move, this pin 65 enters into the groove 30 on the underside of tray T located at the center line of trackway 15 and rearwardly spaced from the pin 52 on the drive block 40 to thereby retain the tray T in its proper position with respect to the trackway 15 so that the vessel V previously ejected may be returned to the same position on said tray T upon completion of the analysis of the fluid samples therein.

As the drive mechanism continues to move the upper run 34a of belt 34 to the left as viewed in FIG. 1, the drive block 40 moves the coupler block 42 and vessel V along the trackway 15 in the "in direction: past work station B and toward work station A.

As vessel V moves through the trackway 15 it is supported upon rail members 15a attached to wall members 70 and 71 and which extend longitudinally along and on opposite sides of the trackway 15.

As the coupler block 42 approaches work station A, it engages roller 73 rotatably supported on the free end 74 of tube carrier arm 75 of elevator assembly 78.

Figure 7:
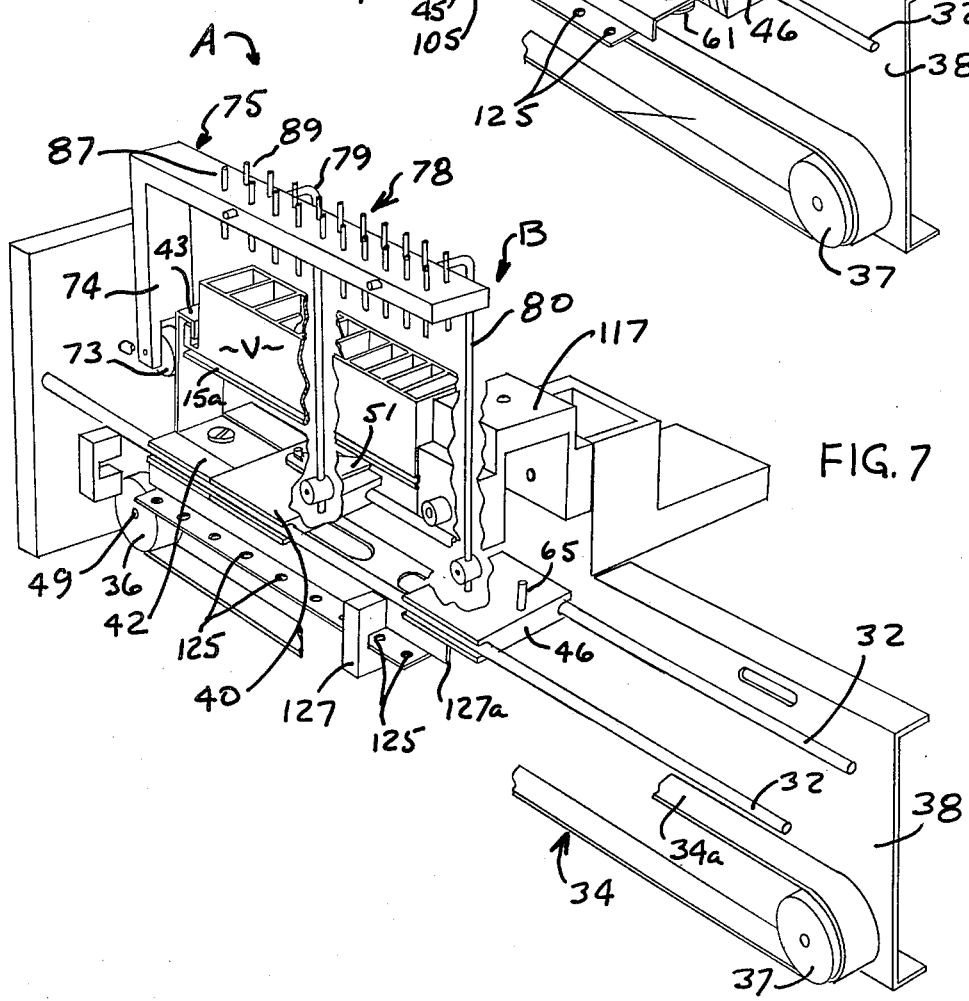
FIG. 7 is a partial side view similar to FIG. 6 and with the forward end of the vessel engaging the elevator assembly to initiate lowering the wash and vacuum tubes or conduits into each cuvette.
Figure 8:
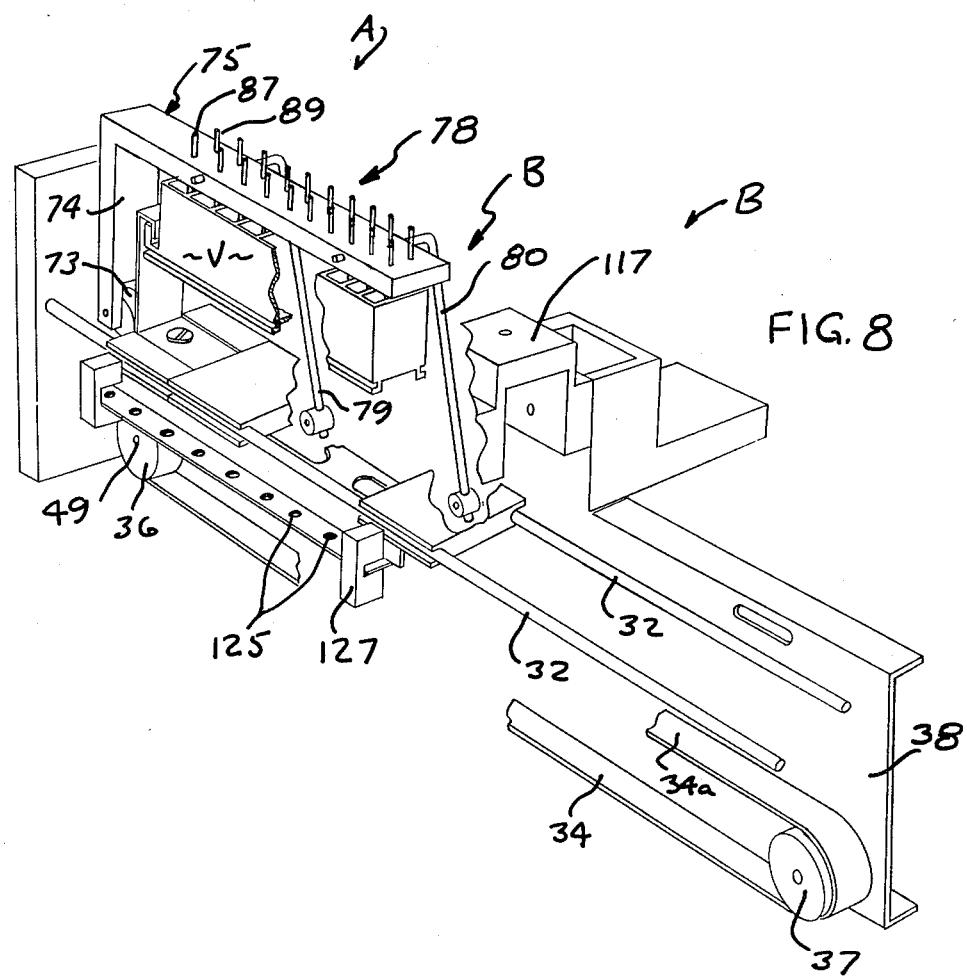
FIG. 8 is a partial side view similar to FIG. 7 and with the cuvette vessel having been moved outwardly from the wash and vacuum station and to the reagent dispensing and measurement stations.

Elevator assembly 78 is swingably supported on wall member 71 by rod elements 79 and 80 defining a parallelogram linkage whereby as the coupler block 42 engages and pushes against roller 73, the tube carrier arm 75 is arcuately swung while maintaining its horizontal position downwardly from its FIG. 7 position and in the "in direction" of the trackway 15 to its FIG. 8 position.

In the present embodiment, carrier arm 75 is provided with two rows of holes 83, 84, the number of holes in each row corresponding to the number of cuvettes in vessel V. It is also contemplated that additional rows of holes or individual holes may also be provided in said carrier arm.

One hole of row 83 is paired with one hole of row 84, and the location of each hole pair is preselected so that it is directly over one of the cuvettes of vessel V when the carrier arm 75 reaches its FIG. 8 position.

One end of a flexible conduit or tube 87 is placed into and secured in each hole 83 as to extend below the carrier arm 75 and in similar fashion one end of a tube 89 is placed into each hole 84.

The opposite end of each tube 87 is connected to a common manifold 91 which, in turn, is connected by conduit 92, coupler 93, and conduit 94 to a vacuum pump 95. Each tube 87 extends below the carrier arm 75 a distance sufficient to enable it to enter into the cuvette located directly therebelow as the carrier arm is moved to its FIG. 8 position and to reach to the bottom of said cuvette.

The opposite end of each tube 89 is connected to the common output of a peristaltic pump identified at 98, the input of said pump being connected by conduit 99 to a reservoir 101 containing a suitable wash media.

Each tube 89 also extends below the carrier arm 75 a distance sufficient to enable it to enter into the cuvette directly therebelow when the carrier arm 75 is moved to its FIG. 8 position.

With this assembly, when the vessel V reaches station A one end of each pair of tubes 87 and 89 is disposed within its associated cuvette. And, by operating the vacuum pump 95 and peristaltic pump 98 at this time by a suitable control logic (not shown) the wash media from reservoir 101 may be injected into each cuvette sufficient to wash out the cuvette interior and if an anti-body material is present therein to wet the same. Likewise, operation of the vacuum pump 95 empties each cell of the wash media. Hence, flush and evacuation of each cell is accomplished individually and concurrently.

It is also contemplated that the control logic may be operable to provide one or more wash and vacuum cycles of operation.

When the work at station A is completed, the control logic may be operable to reversibly actuate the motor and move the upper run 34a of belt 34 in the "out direction" along trackway 15 and result in moving the vessel V to work station B.

To accomplish this, the position indicator plate 45 is formed with a second elongated slot 103 extending longitudinally therealong and into which is freely disposed one end of pin 105 carried on the drive block 40, this interconnection defining a lost motion connection between drive block 40 and said plate 45.

As the drive block 40 is moved by belt 34 in the "out direction" along trackway 15, the pin 105 engages the end of the slot 103, adjacent retainer block 46, and thence moves therewith the position indicator plate 45 and coupler block 42 in the same "out direction". The vessel V is thereby moved along rail member 15a toward station B.

Station B is defined by a bridge assembly 115, straddling the trackway 15 approximately midway therealong and under which passes the vessel V.

As seen in FIGS. 1 and 4, bridge assembly 115 includes a top plate member 117 into which is disposed one end of a flexible conduit 120. The opposite end of conduit 120 is connected to a dispenser unit 121 which, in the present embodiment, is intended to dispense a suitable fluid reagent such as an enzyme substrate solution of the type referred to in the aforementioned publication.

The vessel V is intended to be moved under the plate member 117 and stopped to sequentially locate such cuvette directly under the conduit 120 so that the fluid reagent may be dispensed into the same.

To accomplish this, as best seen in FIGS. 7 and 8, the position indicator plate 45 is formed with a series of position holes 125 spaced longitudinally therealong and corresponding in number to the number of cuvettes in the vessel V.

A sensor 127 is mounted on the wall 127a adjacent the bridge assembly 115, and is operable to sense (read) the position of each position hole 125 as the vessel V moves into the bridge assembly. Each of the holes 125 corresponds in position on the plate 45 to the position of one of the cuvettes in the vessel V, and when a particular cuvette is moved directly under the plate member 117 and conduit 120, the sensor senses this position by means of sensing or reading the corresponding position of its associated position holes 125 and stops the movement of endless belt 34.

In the present embodiment, the sensor 127 is a coupled light emitting detecting device such as a light emitting diode-sensor device mounted on wall 127a so as to scan the path taken by the position holes 125 and which is connectable into the control logic circuitry of the instrument and operable to deactuate the drive motor 48 each time it senses that one of the position holes 125 has reached a predetermined location, and which locates its corresponding cuvette directly underneath the reagent conduit 120.

With the cuvette thus located, the control logic circuitry is actuated to energize the reagent dispenser and to dispense a predetermined quantity of reagent into the cuvette at position B for mixture with the sample fluid therein.

The motor 48 may then be reactivated effective to bring the next cuvette in vessel V under the reagent conduit 120 whereupon reagent is dispensed into the same. This step-by-step advance of the vessel V is continued until all of the cuvettes have reagent dispensed therein.

The present instrument is also intended to provide spectrophotometric analysis of the fluid and reagent mixture.

For this purpose a spectrophotometer assembly is provided which may be of the type disclosed in the assignee's U.S. Pat. No. 3,344,702 and which is capable of measuring the light absorbance of a plurality of fluid samples disposed in individual, separate cuvettes.

The spectrophotometer is located at station B and is generally depicted at 150 wherein it is operable to measure absorbance of the fluid sample located at station B.

Each cuvette is constructed so as to have a window formed on its side wall as depicted at w and which is optically formed to permit the monochromatic light to pass undistorted therethrough and into the cuvette sample fluid.

A suitable conventional absorbance meter 152 may be carried in the instrument cover 153 and in view of the operator to thus provide a visual absorbance reading of the cuvette sample fluid.

It is also contemplated that additional recording means such as a chart recorder of the type referred to in the aforementioned U.S. Pat. No. 3,344,702, may be utilized to provide a printed record of the cuvette readings.

After the last cuvette in the vessel V has been moved to the measuring station B, and the absorbance of the fluid sample therein has been measured, the drive mechanism is again activated to propel the upper run of belt 34a in the "out direction" along trackway 15 to pull the coupler block 42 therealong and return the vessel V back onto the tray T into the channel 19 it previously occupied.

During this interval, the drive block 40 moves against the retainer block 46 and slides it outwardly until its pin 65 is once again spaced away from and in front of the longitudinal edge 55 of tray T.

At the same time, as the drive block 40 moves toward its FIG. 1 position, the plate 51 begins to swing about its pivot 51a under the influence of its spring bias 53 in a counterclockwise direction to return the plate and pin 52 to the position as shown in FIG. 1, whereat it is thus capable of entering into the next successively positioned cam 28 advancing the tray T in the direction F or to the left as viewed in FIG. 1 to bring the next successive vessel V to alignment with trackway 15, whereupon it is thus located to be moved adjacent to the next successive cam 28 on the underside of tray T.

And, upon subsequent actuations of the drive mechanism by the control logic circuitry, whereby the drive block 40 is again moved in the "in direction" along trackway 15, the pin 52 is initially swung by plate 51 clockwise as viewed in FIG. 1 adjacent the said next successive cam 28 whereupon engagement thereof and with the continuation of the movement of drive block 40 advances tray T in the forward direction F along guideway 12 to locate the next vessel V at trackway 15 and directly in front of the instrument.

The original vessel V is thereby moved with tray T out of coupling engagement with the coupler block 42 and is replaced by said next successive vessel V.

The original vessel V may be retained in the tray T until all other vessels on said tray have been analyzed after which all vessels V may be retained, as for example, in a suitable incubation environment for subsequent analysis thereof or said vessels may be discarded.

Alternatively, the operator may remove each vessel V from the tray T after it has been moved away from the instrument trackway 15 whereby it can be individually retained for subsequent analysis or it may also be discarded.

It is also contemplated, that the control logic circuitry may be programmed to merely carry the vessel V to either work station A or B where, for example at station A the cuvettes are simply washed and evacuated and then returned to the tray T. Or said vessel may be moved to station B where reagent is added and/or spectroanalysis thereof is undertaken, and the vessel V is thence returned to tray T.

The instrument of the present invention is provided with suitable operator controls which are connected into the control logic circuitry and which are manually operated to enable the instrument to perform as heretofore explained.

In the present embodiment, these controls are mounted on the front face 166 of the instrument cover 153 as to be easily accessible to the operator, and include from right to left as viewed in FIG. 1, a start button S, read switch R, PRCS (process) pushbutton PR, wash switch W, zero control for absorbance meter, blank pushbutton P for resetting absorbance meter to zero and restart pushbutton RE.

By these controls, the operator may program the instrument to start its cycle to include wash and evacuation of each cuvette in vessel V at station A, and reagent dispensing and spectroanalysis of the fluid sample mixture at station B or alternatively either of the above functions at station A or B.

Having thus described one embodiment of this invention, it will be apparent to one skilled in the art that various modifications and/or changes may be incorporated therein without departing from the inventive concepts as are defined in the claims.

What is claimed is:

1. An apparatus for monochromatically measuring a fluid sample in a cuvette comprising: vessel means each containing at least one cuvette into which is disposed a fluid sample to be analyzed: transfer means for carrying said vessel means to a processing path: conveying means including a drive belt mechanism disposed along said path; first block means connectable with said belt mechanism being movable therewith and operable to move the transfer means in a direction perpendicular to said processing path and to locate said transfer means at one end of said path: means connectable with said first block means and engageable with said transfer means for releasably locking said transfer means at said one end of said path: second block means actuatable by said first block means and movable along said path effective to move the vessel means individually off said transfer means and along the processing path to a first predetermined position thereon: reagent additive means for adding reagent to each cuvette as it is disposed at said first predetermined position on said trackway: analyzing means disposed at said predetermined position alongside the trackway for taking a monochromatic measurement of the fluid sample and reagent solution in each cuvette; and means for positioning each of the cuvettes one at a time in timed sequence opposite the analyzing means to enable the analyzing means to take a monochromatic measurement of the solution in each cuvette.

2. An apparatus as defined in claim 1 and wherein the second block means includes coupling means engageable with the vessel means preparatory to moving the same off the transfer means.

3. An apparatus as is defined in claim 1 and wherein each cuvette is formed with window means optically suitable to enable photometric measurement therethrough.

4. An apparatus for monochromatically measuring a fluid sample in a cuvette comprising vessel means each containing at least one cuvette into which is disposed a fluid sample to be analyzed: transfer means for carrying said vessel means to a processing path: conveying means including a drive belt mechanism disposed along said path; first block means connectable with said belt mechanism being movable therewith and operable to move the transfer means in a direction perpendicular to said processing path and to locate said transfer means at one end of said path: means connectable with said first block means and engageable with said transfer means for releasably locking said transfer means at said one end of said path; second block means actuatable by said first block means and movable along said path effective to move the vessel means individually off said transfer means and along the processing path to a first predetermined position thereon: means at said position for washing and evacuating fluid from each of said cuvettes in said vessel means, said conveying means subsequently moving said vessel means to a second position along said trackway; reagent additive means for adding a reagent to each cuvette as it is disposed at said second predetermined position; analyzing means disposed at said second position for taking a monochromatic measurement of the fluid sample and reagent solution in each cuvette; and means for positioning the cuvettes one at a time in timed sequence opposite the analyzing means to enable the analyzing means to take monochromatic measurements of the solution in each cuvette.

5. An apparatus as defined in claim 4 wherein the means for washing and evacuating includes elevator means carrying conduit means movable into each of the cuvettes in the vessel effective to concurrently and individually wash and evacuate each said cuvettes.

6. An apparatus as is defined in claim 5 and wherein each cuvette of the vessel means may accommodate individually therein a particular antibody which is characteristic of a specific disease under test.

7. An apparatus as is defined in claim 6 and wherein the cuvette is capable of accommodating precise volumes of serums and reagents.

8. An apparatus as defined in claim 5 wherein the elevator means includes means engageable by the conveying means effective to initiate operating the elevator means and to effect movement of the conduit means into and out of the cuvettes.

* * * * *